US011058814B2

United States Patent
Li et al.

(10) Patent No.: US 11,058,814 B2
(45) Date of Patent: Jul. 13, 2021

(54) MICRO DELIVERY DEVICE

(71) Applicant: MicroMED Co., Ltd., Taipei (TW)

(72) Inventors: Po-Ying Li, Taipei (TW); Tsung-Chieh Cheng, Kaohsiung (TW); Chia-Chi Feng, Taipei (TW)

(73) Assignee: MICROMED CO., LTD., Taipei (TW)

( * ) Notice: Subject to any disclaimer, the term of this patent is extended or adjusted under 35 U.S.C. 154(b) by 44 days.

(21) Appl. No.: 15/785,798

(22) Filed: Oct. 17, 2017

(65) Prior Publication Data

US 2018/0104408 A1  Apr. 19, 2018

Related U.S. Application Data

(60) Provisional application No. 62/409,067, filed on Oct. 17, 2016.

(51) Int. Cl.
*A61M 5/142* (2006.01)
*A61L 31/04* (2006.01)
(Continued)

(52) U.S. Cl.
CPC ........ *A61M 5/14276* (2013.01); *A61L 31/04* (2013.01); *A61L 31/08* (2013.01); *A61L 31/14* (2013.01); *A61M 5/14224* (2013.01); *A61M 5/158* (2013.01); *A61L 2400/16* (2013.01); *A61M 2005/14204* (2013.01); *A61M 2205/0216* (2013.01); *A61M 2205/3303* (2013.01); *A61M 2205/3337* (2013.01); *A61M 2205/587* (2013.01)

(58) Field of Classification Search
CPC .... A61M 2005/14204; A61M 5/14276; A61M 5/14244; A61M 5/14586; A61M 5/14593
See application file for complete search history.

(56) References Cited

U.S. PATENT DOCUMENTS 4,443,218 A * 4/1984 DeCant, Jr. ........ A61M 5/14276
128/DIG. 12
6,440,120 B1 * 8/2002 Maahs .................... A61F 2/013
604/264
(Continued)

FOREIGN PATENT DOCUMENTS

JP   2009-517160 A   4/2009
JP   2015-502785 A   1/2015
(Continued)

*Primary Examiner* — Bhisma Mehta
*Assistant Examiner* — James D Ponton
(74) *Attorney, Agent, or Firm* — Birch, Stewart, Kolasch & Birch, LLP (57) ABSTRACT

The present invention provides a delivery device which comprises a substrate, a rigid shell a diaphragm, a cannula, an electrode and an electronic device chamber. The substrate has a first side and a second side. The second side is opposite to the first side. The rigid shell is disposed on the first side of the substrate. A chamber is defined by the rigid shell and the substrate. The diaphragm is configured within the chamber to divide the chamber into an upper reservoir and a lower reservoir. The cannula penetrating through the rigid shell and in fluid communication with the upper reservoir. The electrode is disposed on the first side of the substrate. The electronic device chamber is electrically connecting to the electrode.

22 Claims, 11 Drawing Sheets

(51) Int. Cl.
*A61L 31/08* (2006.01)
*A61L 31/14* (2006.01)
*A61M 5/158* (2006.01)

(56) References Cited

U.S. PATENT DOCUMENTS

| | | | |
|---|---|---|---|
| 2002/0120186 A1* | 8/2002 | Keimel | A61B 5/14865 600/365 |
| 2005/0055014 A1* | 3/2005 | Coppeta | A61K 9/0009 604/890.1 |
| 2006/0255064 A1* | 11/2006 | Donaldson | A61M 5/142 222/95 |
| 2007/0043335 A1* | 2/2007 | Olsen | A61M 5/14276 604/890.1 |
| 2008/0288026 A1 | 11/2008 | Cross et al. | |
| 2009/0017225 A1* | 1/2009 | Janssen | A61N 1/303 427/560 |
| 2009/0306594 A1* | 12/2009 | Pang | A61F 9/00781 604/133 |
| 2010/0061870 A1 | 3/2010 | Cannell et al. | |
| 2011/0060280 A1 | 3/2011 | Caffey et al. | |
| 2011/0202032 A1* | 8/2011 | Shih | A61M 5/14593 604/500 |
| 2011/0275410 A1 | 11/2011 | Caffey et al. | |
| 2013/0030255 A1* | 1/2013 | Embry, II | A61B 5/686 600/300 |
| 2013/0096503 A1* | 4/2013 | Haase | A61M 5/16809 604/152 |
| 2013/0184640 A1* | 7/2013 | Li | A61M 5/14526 604/67 |
| 2014/0214010 A1* | 7/2014 | Kuo | A61M 5/14276 604/891.1 |
| 2014/0296784 A1 | 10/2014 | Lopez | |
| 2014/0371674 A1* | 12/2014 | Wang | A61L 31/14 604/140 |
| 2014/0374245 A1* | 12/2014 | Dunn | C25B 15/08 204/275.1 |
| 2015/0011940 A1 | 1/2015 | Chappel et al. | |
| 2015/0250919 A1* | 9/2015 | Kettlewell | A61L 15/60 604/368 |
| 2016/0206811 A1 | 7/2016 | Shih et al. | |
| 2016/0220753 A1* | 8/2016 | Ambrosina | A61M 5/1407 |
| 2017/0020416 A1* | 1/2017 | Scherer | A61B 5/1473 |

FOREIGN PATENT DOCUMENTS

| | | |
|---|---|---|
| JP | 2015-509764 A | 4/2015 |
| JP | 2016-517717 A | 6/2016 |
| WO | WO 2013/075109 A2 | 5/2013 |

* cited by examiner

MICRO DELIVERY DEVICE

CROSS REFERENCE TO RELATED APPLICATIONS

This non-provisional application claims the benefit under 35 U.S.C. § 119(e) to U.S. Provisional Application No. 62/409,067, filed on Oct. 17, 2016, all of which are hereby expressly incorporated by reference into the present application.

FIELD OF THE INVENTION

The present invention is related to a delivery device, in particular to a micro delivery device for use in delivering a therapeutic agent to a target location within living tissues.

BACKGROUND OF THE INVENTION

Recently, minimized delivery pumps of therapeutic agents have been proposed to improve the issues in pharmaceutical industry. However, some deficiencies still waiting to be improved for conventional designs on delivery pumps of therapeutic agents. For example, dose inaccuracy and pump reliability caused by permanent material deformation of thin reservoir elastic shell, low pump energy efficiency for the thin reservoir elastic shell due to gas escaping/recombination with the permanent elastic shell material expansion, the cross-contamination when refilling a therapeutic agent into the reservoir via two filling ports in conventional designs, residual air bubbles which may cause some concerns while delivering the air into small animals which are less tolerated to air in blood stream, the degree of accuracy when controlling the dose of the therapeutic agent, and de-bonding of a cannula when the cannula delivers the therapeutic agent from the reservoir to the target being treated, etc.

A need therefore exists for apparatus and methods to be improved and to solve the above-mentioned pending problems.

SUMMARY OF THE INVENTION

In various embodiments, the present invention relates to an improved and simplified micro delivery device for delivering a therapeutic agent to a target location within living tissues.

Accordingly, one aspect of the invention pertains to a micro delivery device. The micro delivery device includes a substrate, a rigid shell a diaphragm, a cannula, an electrochemical pump comprising at least one electrode and an electronic device chamber. The substrate has a first side and a second side. The second side is opposite to the first side. The rigid shell is disposed on the first side of the substrate. A chamber is defined by the rigid shell and the substrate. The diaphragm is configured within the chamber to divide the chamber into an upper reservoir and a lower reservoir. The cannula penetrating through the rigid shell and in fluid communication with the upper reservoir. The electrode is disposed on the first side of the substrate. The electronic device chamber is electrically connecting to the electrode.

In one embodiment of the present invention, the micro delivery device further comprises a port penetrating through the rigid shell and in fluid communication with the upper reservoir.

In one embodiment of the present invention, the chamber can be divided into a plurality of sub-chambers.

In one embodiment of the present invention, the electrode includes not less than three electrodes, two of the electrodes are applied as positive and negative, one of the electrodes is applied as a reference electrode to prevent IR drop, and other electrodes are used as redundant electrodes to prevent from inconvenience of repairing whenever a sudden malfunction of an electrode occurs.

In one embodiment of the present invention, the electrode is hydrophilic.

In one embodiment of the present invention, a superabsorbent material is attached to the surface of the electrode.

In one embodiment of the present invention, the superabsorbent material is made of a material selected from PVA poly(vinyl alcohol), PEO poly(ethylene oxide), poly(acrylic acid), PLA (polylactic acid), PGA (polyglycolic acid), PLA/PGA (copolymers) and PCL (polycaprolactone).

In one embodiment of the present invention, the electronic device chamber is configured on the second side of the substrate.

In one embodiment of the present invention, the electronic device chamber is configured on the first side of the substrate.

In one embodiment of the present invention, the electronic device chamber comprises a printed circuit board, a power supply, a triggering device, and an elastic contactor, the elastic contactor being electrically connecting the printed circuit board to the substrate, the power supply being electrically connected to the printed circuit board, and the triggering device being electrically connected to the printed circuit board.

In one embodiment of the present invention, the electronic device chamber is a demountable electronic device chamber.

In one embodiment of the present invention, the rigid shell is transparent.

In one embodiment of the present invention, the substrate is transparent.

In one embodiment of the present invention, the rigid shell is made of a material selected from PEEK, polycarbonate, parylene, polypropylene, PE, epoxy, PS, PU, ABS, PMMA, PTFE, Teflon, PF, polyimide, PLA, silicone, metals and its alloys (titanium, stainless steel, gold, platinum, siliver, aluminum), and glass.

In one embodiment of the present invention, the substrate is made of a material selected from silicon, metals and its alloys (titanium, stainless steel, gold, platinum), silicone, parylene, and plastics (PEEK, polycarbonate, parylene, polypropylene, PE, epoxy, PS, PU, ABS, PMMA, PTFE, Teflon, PF, polyimide, and PLA), and glass.

In one embodiment of the present invention, the substrate is flexible.

In one embodiment of the present invention, the substrate is rigid.

In one embodiment of the present invention, the diaphragm has a helically corrugated structure.

In one embodiment of the present invention, the diaphragm further comprises a bellow.

In one embodiment of the present invention, the diaphragm is flattened and made of super-elastic materials.

In one embodiment of the present invention, the diaphragm comprises a bellow and a propulsion plate.

In one embodiment of the present invention, the micro delivery device is coated with a gel-like coating.

In one embodiment of the present invention, the electrode is made in the shape of inverse-trapezoid.

In one embodiment of the present invention, the electronic device chamber further comprises a filler block, and the filler block fills the empty space of the electronic device chamber.

In one embodiment of the present invention, a side wall of the cannula has corrugated structures for releasing stress induced from the movement of the micro delivery device.

In one embodiment of the present invention, the micro delivery device further comprises a check valve in the cannula or the rigid shell.

In one embodiment of the present invention, the micro delivery device comprises a single port.

In one embodiment of the present invention, the elastic contactor is a Pogo Pin.

These and other objects, along with advantages and features of embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Unless defined otherwise, all technical and scientific terms used herein have the same meaning as commonly understood by a person skilled in the art to which this invention belongs.

A subject can be human, animal such as mouse, rat, rabbit, pig, dog, and more (not limited to the terms mentioned here).

The word "a" or "an" as used herein means "at least one".

Body part of a subject can be subcutaneous, intraocular, inner ear, and intracranial (these are just few examples and not only limited to these cases).

In general, most embodiments of the present invention pertain to a micro delivery device for delivering therapeutic agents to the body part of a subject.

Figure 1:
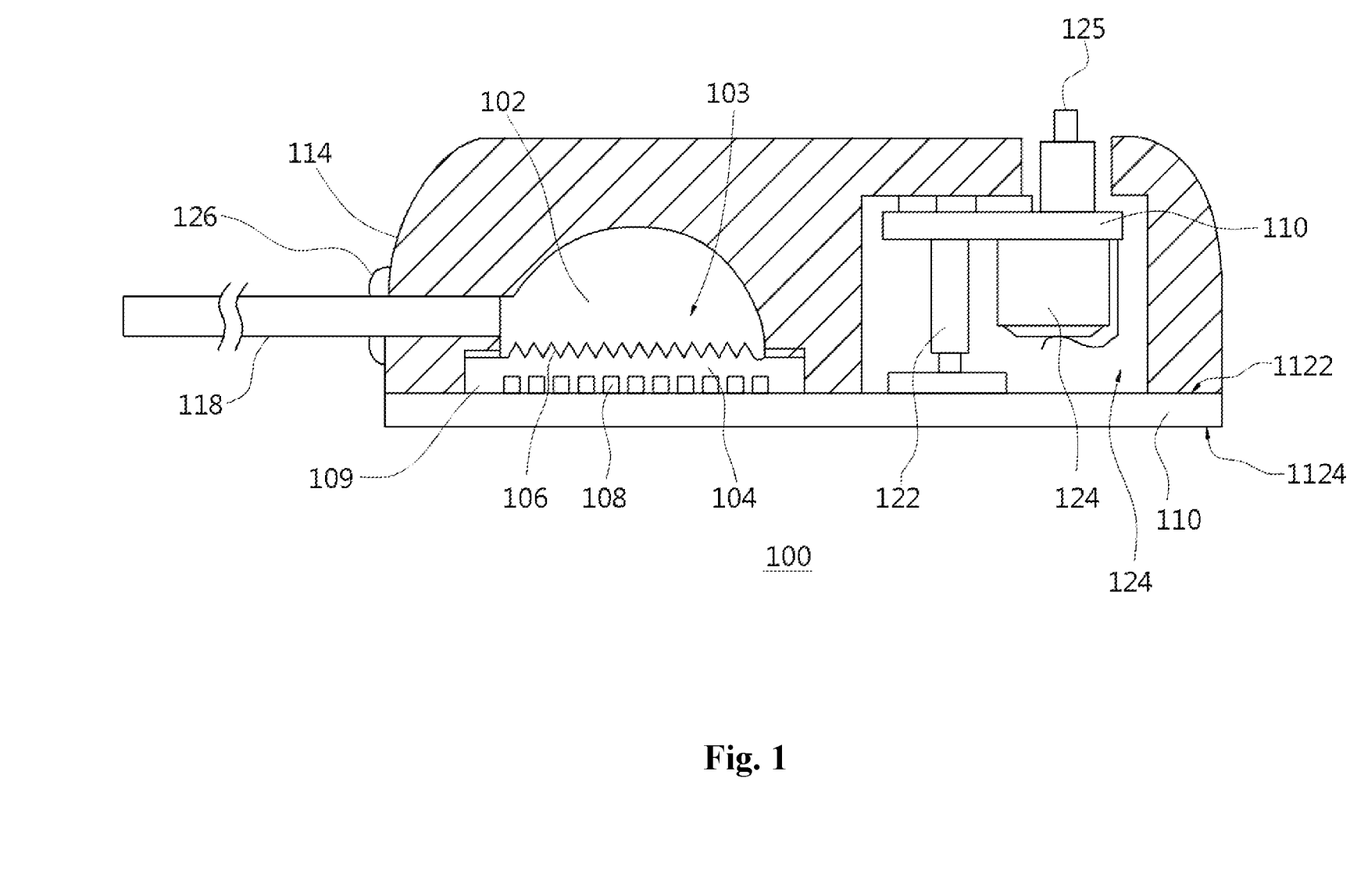
FIG. 1 is a cross-sectional view of a portless micro delivery device according to one embodiment of the present invention.

FIG. 1 provides the cross-sectional view of a portless micro delivery device as one embodiment of the present invention.

A preferred embodiment of the present invention discloses a micro delivery device 100. The micro delivery device mainly includes a substrate 112, a rigid shell 114, a diaphragm 106, a cannula 118, an electrochemical pump comprising an electrode 108, and an electronic device chamber 110. The substrate 112 has a first side 1122 and a second side 1124, wherein the second side 1124 is opposite to the first side 1122. The substrate 112 can be made of biocompatible materials, such as glass in this embodiment. The rigid shell 114 is disposed on the first side 1122 of the substrate 112 whereby the rigid shell 114 and the substrate 112 define a chamber 103.

The diaphragm 106 is configured within the chamber 103 to divide the chamber 103 into an upper reservoir 102 and a lower reservoir 104. In this preferred embodiment, the upper reservoir 102 is a reservoir 102 configured to store a certain dose of a therapeutic agent. In a preferred embodiment, the micro delivery device 100 is tiny enough to be implanted into the body part of a subject, rendering the dose to be microliter scale in its volume.

In this preferred embodiment, the cannula 118 penetrates through the rigid shell 114 and in fluid communication with the upper reservoir 102. The cannula 118 is used to deliver the therapeutic agent from the upper reservoir 102 to the target for treatment (e.g. subcutaneous tissues in human body or animals, intracochlear locations of diseases, etc.).

In this preferred embodiment, the electrode 108 is disposed on the first side 1122 of the substrate 112 whereby the electrode 108 is within the lower reservoir 104. The electronic device chamber 110 is electrically connected to the electrode 108. Accordingly, the lower reservoir 104 can be regarded as an electrolysis chamber in this preferred embodiment, wherein the electrolysis chamber can be filled with electrolyte 109. The electrolyte 109 used herein can be water or salt solution, but should not be limited herein.

In a particular embodiment, the electronic device chamber 110 of the micro delivery device 100 further includes a printed circuit board 120, a power supply 124, a triggering device 125, and an elastic contactor 122. The elastic contactor 122 electrically connects the printed circuit board 120 to the substrate 112. The power supply 124 is electrically connected to the printed circuit board 120. The triggering device 125 is electrically connected to the printed circuit board 120 and further electrically connected to the power supply 124 in order to control on-off of the power supply 124.

In a preferred embodiment, the electrode 108 includes not less than three electrodes. Specifically, two of the electrodes are applied as positive (+) and negative (−). For better performance on electrolysis, the positive (+) and negative (−) electrodes are arranged in the geometry of a grating. The third electrode plays the role of a reference electrode in order to prevent IR drop (the ohm voltage that results from the electric current flowing in ionic electrolytes, such as dilute acids, salt water . . . etc. IR drop is an unwanted quality which must be eliminated to obtain an accurate potential measurement). The remaining electrodes are used as redundant electrodes, such as a 4Th electrode and a 5th electrode.

The redundant electrodes can prevent from inconvenience of repairing whenever a sudden malfunction of an electrode occurs. The number of electrodes designed in the invention can be customized for real applications.

Referring to FIG. 1 providing a preferred embodiment, the electronic device chamber 110 is configured on the first side 1122 of the substrate, which is electrically connected to the electrode 108 in the lower reservoir 104 via the substrate 112. Besides, the electronic device chamber 110 is osmotically isolated from the lower reservoir 104 and osmotically isolated from the upper reservoir 102.

Additionally, according to this embodiment, the micro delivery device 100 has no port 116. A method for refilling the micro delivery device 100 with a therapeutic agent comprising: inserting a syringe into the upper reservoir 102 through the cannula 118; withdrawing the therapeutic agent left and air inside the upper reservoir 102; and then extracting the syringe from the upper reservoir 102; pre-filling a refilling-syringe with the therapeutic agent; inserting the refilling-syringe into the upper reservoir 102 through the cannula 118 and then filling the therapeutic agent into the upper reservoir 102, and extracting the refilling-syringe from the upper reservoir 102 through the cannula 118 after filling the therapeutic agent.

Figure 2:
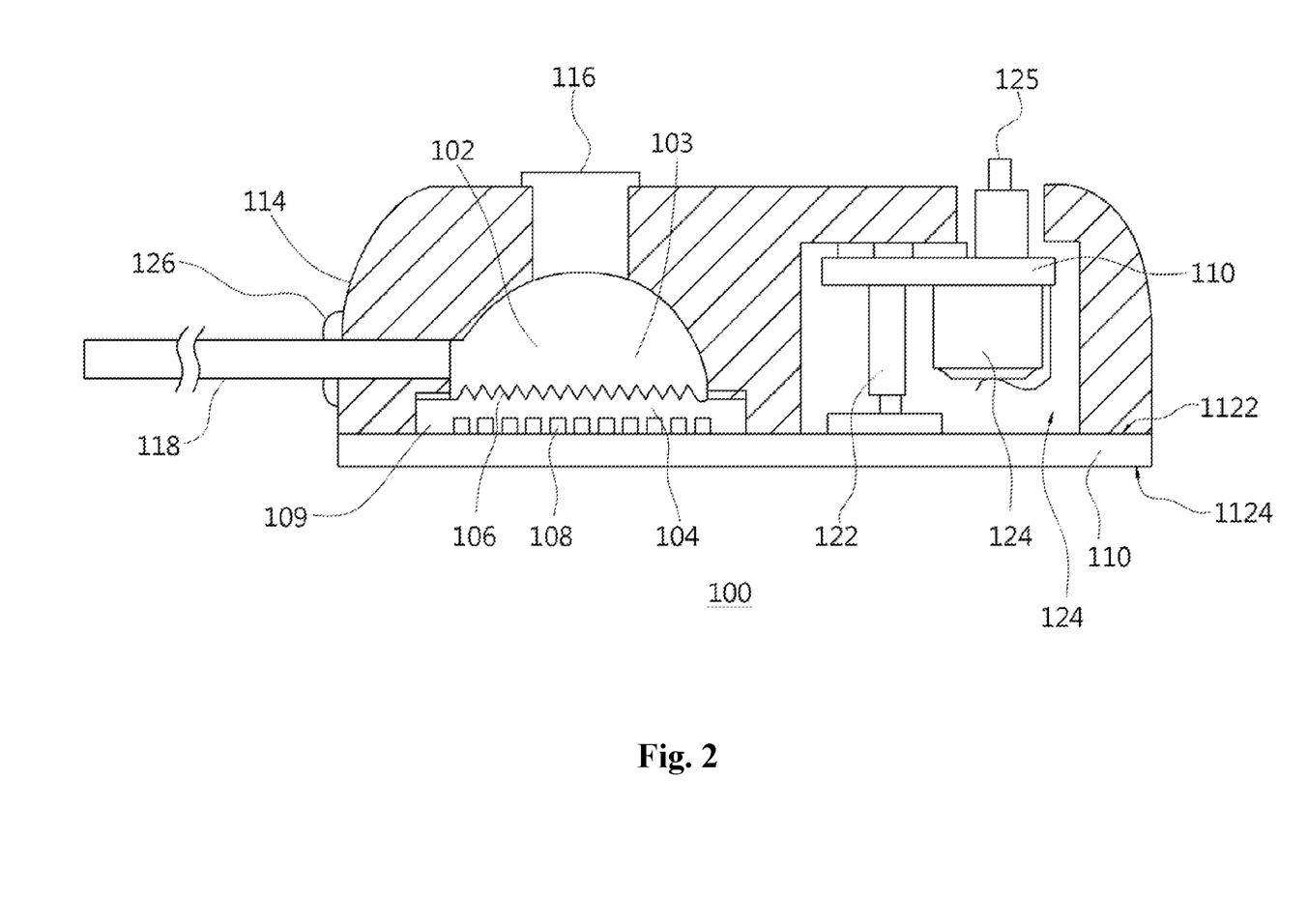
FIG. 2 is a cross-sectional view of a micro delivery device with a port according to one embodiment of the present invention.

FIG. 2 provides the cross-sectional view of a micro delivery device design with a port as another embodiment of the present invention.

Referring to FIG. 2, this embodiment presents a micro delivery device with a port 116 comparing to the previous embodiment. The micro delivery device mainly includes a substrate 112, a rigid shell 114, a diaphragm 106, a port 116, a cannula 118, an electrochemical pump comprising an electrode 108, and an electronic device chamber 110. The substrate 112 has a first side 1122 and a second side 1124, wherein the second side 1124 is opposite to the first side 1122. The substrate 112 can be made of bio-compatible materials, such as glass in this embodiment. The rigid shell 114 is disposed on the first side 1122 of the substrate 112 whereby the rigid shell 114 and the substrate 112 define a chamber 103.

The upper reservoir 102, the lower reservoir 104, and the electronic device chamber 110 are configured to be formed by one single rigid shell 114 (wherein the three spaces are defined merely by the rigid shell 114 and the substrate 112). The unique structural design provides many advantages. For example, it is a low-cost design to incorporate major components of the micro delivery device 100. In addition, it is easy for manufacturing because of the simplified structure with fewer components.

In another embodiment, the substrate of the micro delivery device is flexible. The micro delivery device includes a rigid shell, a flexible substrate, a flexible electrode and a flexible circuit board, but should not be limited herein. The flexible electrode 208 can be made of flexible materials such as plastic or rubber. In this embodiment, the flexible micro delivery device can match the shape of the implanted tissue surface, such that the unwanted tissue response such as scar tissue growth, irritations, or inflammations can be prevented. In addition, patients or animals will be more comfortable with the implanted flexible micro delivery device.

In embodiments of the invention which is a flexible micro delivery device, different manifestations on electrodes can be used, and one can also fabricate flexible electrodes by applying conductive polymers. The micro delivery device comprises flexible electrodes combined with a flexible substrate becomes more flexible. Since most types of conductive polymers are transparent, it can also enhance merits of this invention.

According to the invention, the micro delivery device 100 features the single port 116 (single-port design) configured to refill and/or withdraw the therapeutic agent left and air, and then evacuate the upper reservoir 102. The method for refilling the therapeutic agent via the single port of the micro delivery device of the invention comprises the following steps: (1) inserting a syringe through the port 116 into the reservoir 102 to withdraw the therapeutic agent left and air inside the upper reservoir 102; (2) after the upper reservoir 102 is completely emptied, extracting the syringe from the upper reservoir 102; (3) prefilling a refilling syringe with a therapeutic agent (up to the end of the needle tip), (4) inserting the refilling syringe into the upper reservoir 102 through the port 116 to fill in a specified dosage of the therapeutic agent, and (5) after the filling the therapeutic agent, extracting the refilling syringe from the upper reservoir 102.

In another embodiment, a syringe integrated with a two-way valve may be replaced for the syringe in the above-mentioned singe-port micro delivery device. In this configuration, the withdrawing and refilling of the therapeutic agent can be performed without changing syringes. One way of the two-way valve is to withdraw the therapeutic agent/air from, and refill the therapeutic agent into the upper reservoir 102 through the single port, and the other way is used to pre-fill the syringe with the therapeutic agent while.

The novel strategy on filling the therapeutic agent with single port method mentioned above is designed to give much improved residual air bubble size (nearly zero refilling bubbles in which volumes of bubbles can be controlled by the applied vacuum level) and to withdraw the therapeutic agent left thoroughly so that the therapeutic agent left can be completely removed to lower the variation), which provides improved efficacy as compared with two ports (one for loading in the therapeutic agent in and the other for removing the therapeutic agent out). The design also saves half of the reservoir occupied by ports. Furthermore, the problem of cross-contamination when simultaneously piercing two syringes into the reservoir 102 can be improved in this single port refilling process.

In another embodiment, multiple reservoirs and electrolysis chambers can be integrated into a single pump design. The cannulas of the pump can be independent or connecting in serial/parallel according to the needs of the therapeutic agent delivery. These integrated pumps can be activated individually or concurrently according to the requirement of the therapeutic agent delivery.

Figure 3:
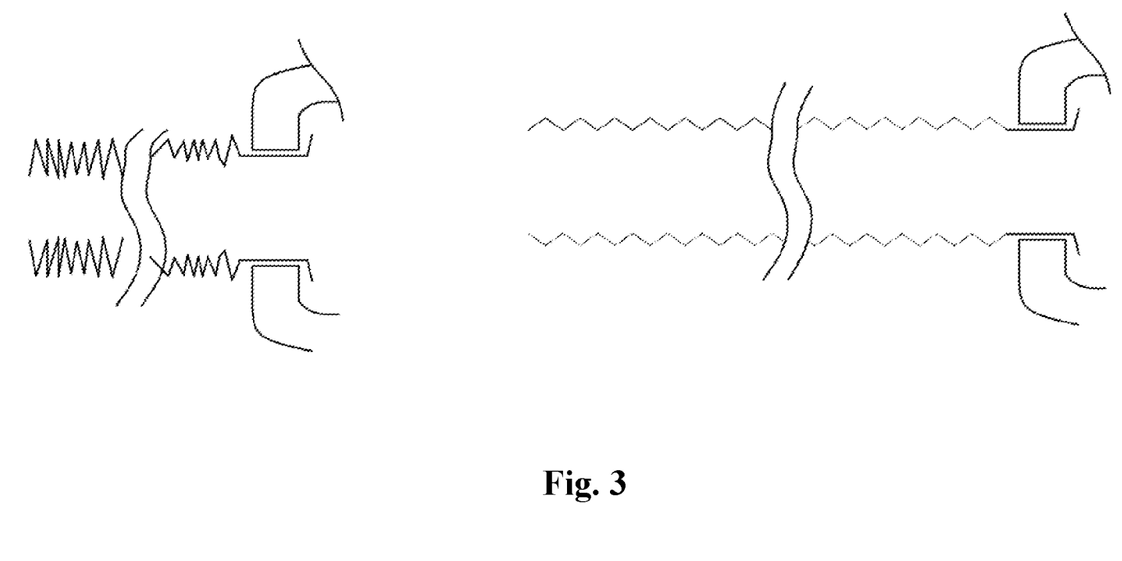
FIG. 3 is a schematic diagram of a cannula in one embodiment of the present invention.

Referring to FIG. 3, provided is a schematic diagram of a cannula in one embodiment of the present invention, a side wall 1182 of the cannula 118 is constructed to have corrugated structures. The corrugated structures herein can release stress induced from the movement of the micro delivery device 100, thus preventing the dropping out of the cannula 118 at the joint position between the cannula 118 and the rigid shell 114. The material used herein on the cannula 118 should be biocompatible and medical stable, such as rubbers (e.g. silicone rubber, nature rubber), polymers (e.g. PE, PP, PS, PMMA, parylene), glasses, metals, and alloys (e.g. stainless steel, titanium, gold). However, in another embodiment, the cannula can also exhibit soft tube with smooth surface thereon. Materials and shapes of the cannula should not be limited herein.

Referring to FIG. 2, a check valve 126 is further installed in the passageway of the cannula or in the rigid shell to prevent body fluids backflow into the upper reservoir 102 and contaminate the therapeutic agent. The inverse breaking pressure of the check valve 126 is chosen to be much higher than maximum pressure difference between the upper reservoir 102 and the portions with body fluids outside the micro delivery device 100, rendering no risk of back-flow.

Figure 4:
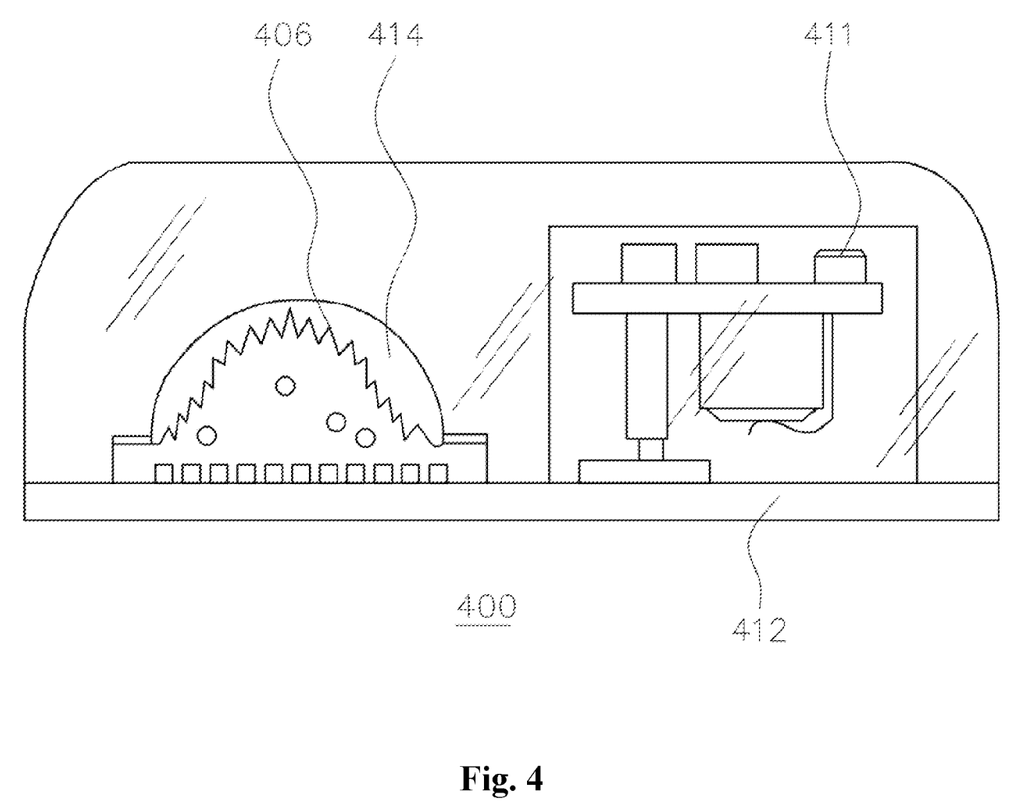
FIG. 4 is a schematic cross-sectional diagram of a transparent micro delivery device in one embodiment of the present invention.

Referring to FIG. 4 providing the schematic cross-sectional diagram of a transparent micro delivery device in one embodiment of the present invention, the micro delivery device 400 can be made of transparent or translucent materials, rendering a transparent rigid shell 414, a transparent substrate 412, and even a transparent diaphragm 406. These transparent/translucent components can be made of glasses (e.g. quartz, fused silica, soda lime, silicate, and borosilicate), polymers/plastics (e.g. polycarbonate (PC), acrylic (PMMA), polypropylenes (PP), polyethylene (PE), PET, PLA, TPE, and parylene), rubbers (nature rubber and silicone rubber), glues (epoxy, silicone gel, and acrylic), and conductive polymers (poly(fluorene)s, polyphenylenes, polypyrens, polyazulenes, polynaphthalenes, PPY, PAM, PT, PEDOT, PPS, PAC, and PPV).

By using the above-mentioned transparent/translucent materials (but should not be limited herein), the performance of a micro delivery device (rigid or flexible) can be understood thoroughly in real time. Furthermore, an indicator 411 such as LED can be installed in the transparent micro delivery device 400. The indicator can provide signals (e.g. illumination) to help physicians to find out the location of the port (such as port 116 in FIG. 2) which is usually buried subcutaneously. Moreover, the transparent/translucent appearance allows special optical sources been installed in a micro delivery device for physiological signal sensing or measurement, and a tissue/disease imaging can also be taken in vivo (e.g. animals and human bodies).

Since many bonding processes are involved in component assembly, the transparent appearances can make manufacturing easier as the bonding result can be observed by simply watching the bonding position, and the flowing of glues into bonding lines/gaps can be seen in easier way. In addition, the filling status of the therapeutic agent, both before and after implant, can be verified and compared to have deeper understanding on how the micro delivery device works and how the living body responds to the injection of the therapeutic agent. Finally, by integrating with a marker for the therapeutic agent (e.g. fluorescent light), the therapeutic agent can be observed and measured through the skin of a living body.

Figure 5:
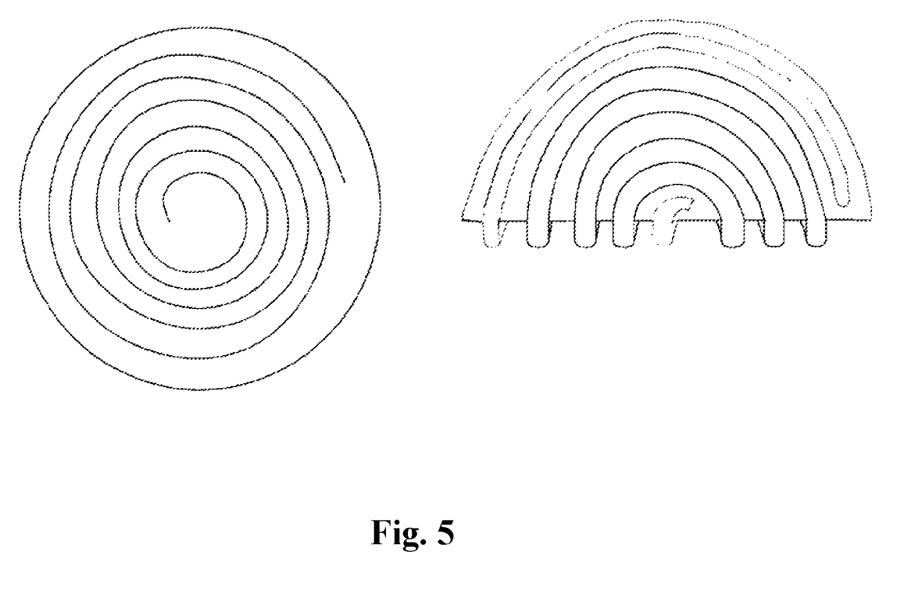
FIG. 5 is a schematic diagram of a diaphragm in one embodiment of the present invention.
Figure 6:
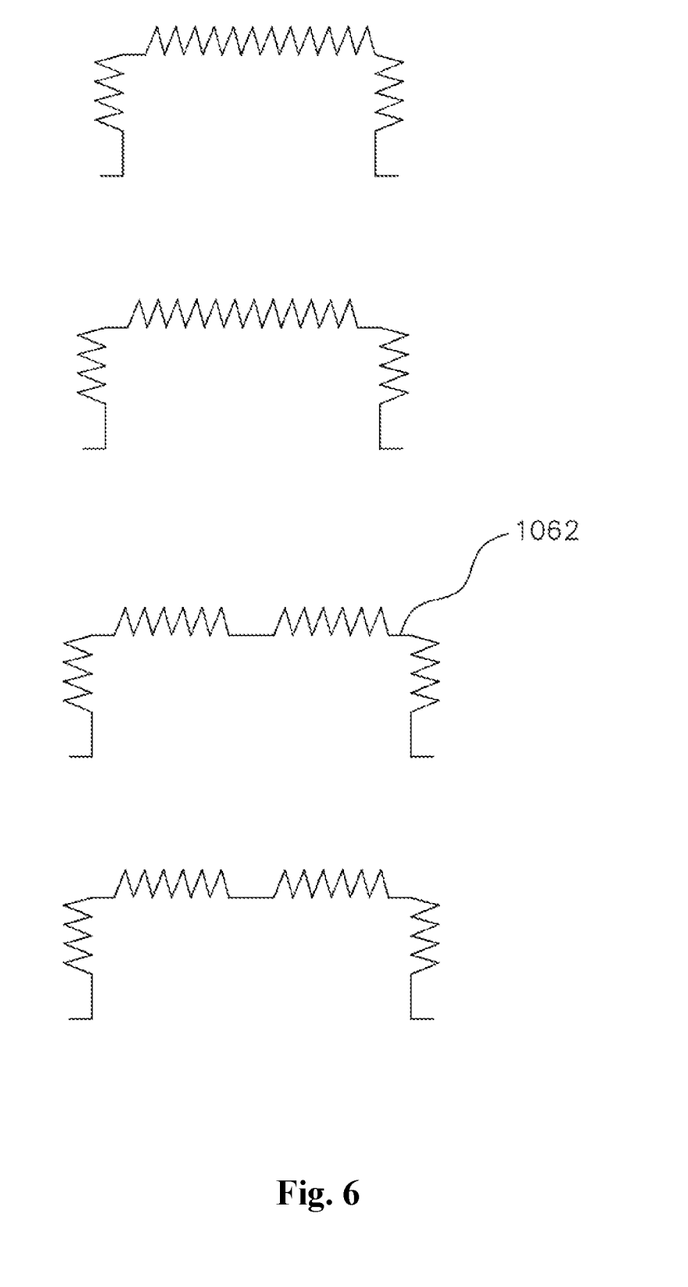
FIG. 6 is a schematic diagram of a diaphragm in another embodiment of the present invention.

Back to the preferred embodiment, the diaphragm 106 in the micro delivery device 100 can be made of a biocompatible material selected from the group consisting of TPE, SEBS, SEPS, and parylene (but not limited to these materials). FIG. 5 and FIG. 6 provides schematic diagrams of two designs of diaphragm in two embodiments of the present invention. Referring to FIG. 5 providing one preferred embodiment, the diaphragm 106 has a helically corrugated structure. Corrugations of the helically corrugated diaphragm are made in one piece throughout the entire diaphragm, whereas in conventional designs the corrugated structure is made of discretely concentric circles.

The helically corrugated diaphragm with corrugations made in one piece can lead to minimal dead volume comparing to conventional diaphragms with corrugations designed to exhibit concentric structures thereon. The difference becomes significant especially when the diaphragm is pushed to the top of the upper reservoir 102. The minimal dead volume can also lead to minimal amount of the therapeutic agent left at the end of the delivery of the therapeutic agent. As a result, the lifetime of the micro delivery device 100 can be extended comparing to conventional designs. It is worth mentioning that, if helical corrugations further combine with bellows thereon, the modified diaphragm 1062 can lead to even better performance on minimizing dead volumes in this embodiment. In another embodiment, the helical corrugations can also hybrid with other corrugations with different shapes.

The helical corrugations on the diaphragm mentioned above is crucial in real applications since the dead volume can seriously shorten the lifetime of the upper reservoir 102 (i.e. the reservoir for a therapeutic agent in this embodiment). The reason is that the therapeutic agent left will stay inside the reservoir due to dead volume and cannot be evacuated during the refill cycle, thus bringing about serious problems on sterility and long-term safety for the whole micro delivery device 100, especially during the treatment of a chronic disease.

In another modified embodiment, the diaphragm 106 is made of super-elastic materials. Super-elastic materials include metal alloys (e.g. copper-zinc-aluminum, copper-aluminum, and nickel-titanium), super-elastic rubber (e.g. synthetic rubber, nature rubber, silicone rubber), and super-elastic polymers for example. The benefit of applying super-elastic materials as a diaphragm is that the flat geometry of the diaphragm can have good performance on expansion, and thus saving cumbersome procedures such as manufacturing corrugated shapes mentioned in previous embodiment. In addition, due to the extreme flexibility of super-elastic diaphragms, the power of electrolysis to trigger the expansion of the diaphragm can be largely reduced comparing to conventional ways by using common flat diaphragms. Thus, with novel materials having super-elastic nature, the diaphragm in this embodiment can still have good performance on expansion even by applying low gas pressure comparing to that applied on conventional flat diaphragms. The super-elastic diaphragm disclosed herein is easy to fabricate, low cost, and convenient to be incorporated into the micro delivery device 100.

Figure 7:
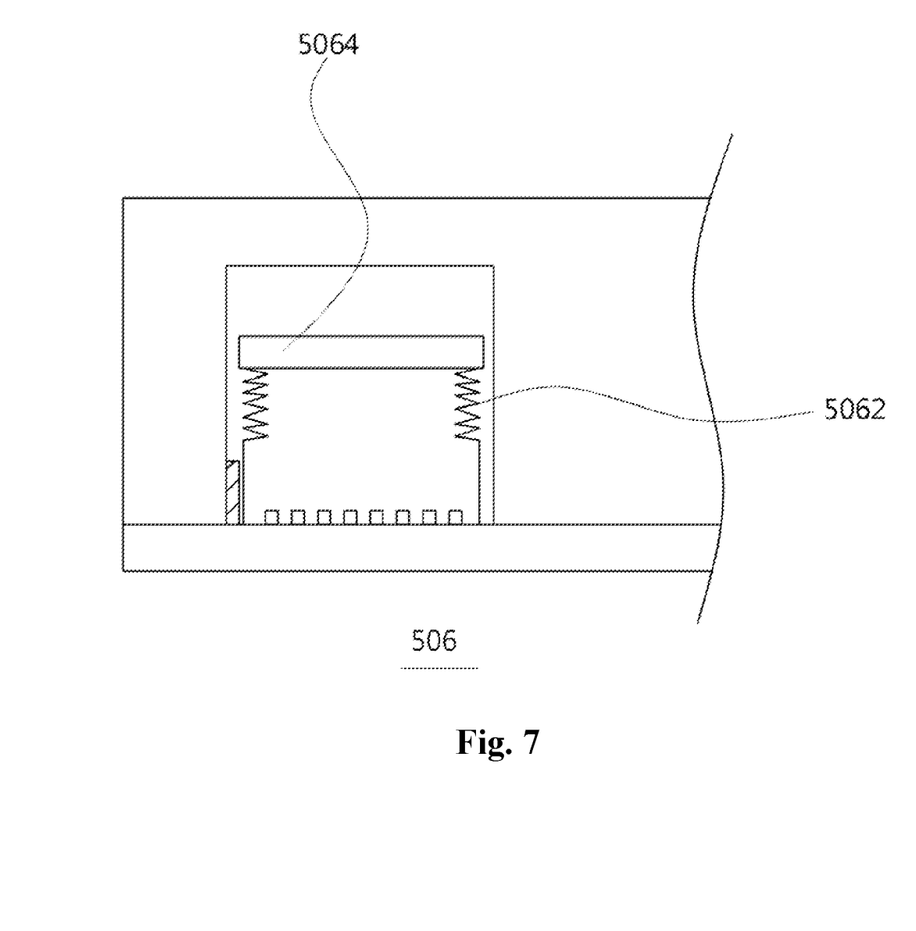
FIG. 7 is a schematic cross-sectional diagram of a diaphragm in one further embodiment of the present invention.

Referring to FIG. 1 and FIG. 7 providing a schematic cross-sectional diagram of another design of diaphragm in one embodiment of the present invention, the diaphragm 506 can include a bellow 5062 and a propulsion plate 5064. The bellow 5062 is hermetically connected to the propulsion plate, and the bellow 5062 and the propulsion plate 5064 enclose the electrode 108 and the electrolyte 109 to define the lower reservoir 104 (electrolysis chamber in this embodiment). Due to geometry of the design, the structure of this combinative diaphragm 506 can have even less (close to zero) dead volume if the shape of a rigid shell is designed corresponding to the shape of the propulsion plate 5064, leading to near zero therapeutic agent/electrolyte cross contaminations.

Considering comfort feelings for living ones (e.g. animals or patients), a coating on a micro delivery device is introduced herein. A coated micro delivery device is coated with a gel-like layer thereon. The configuration of the micro delivery device can be any structures mentioned in other paragraphs in this disclosure. The gel-like layer can be made of biocompatible materials such as silicone rubber, but should not be limited herein. Deposition methods can be dip coating, spray coating, vacuum depositions (e.g. chemical vapor deposition, CVD), and vaporized coating.

With the coated micro delivery device, sharp corners, rough edges, and hard surfaces on the micro delivery device are smoothened due to the coated layer. The smoothened geometry and texture can comfort living ones when the coated micro delivery device is implanted and stay within tissues. The design also leads to less rubbing and scrubbing against tissues inside living ones.

In yet another embodiment, the electrode 108 and its substrate can be coated to improve electrolysis efficiency during pumping periods. Specifically, hydrophilic materials such as PVP, PAA, PEO, polysaccharides, nafion, nanostructural metals, and epoxy are preferable for coating. The reason for applying hydrophilic coating on the surface of the electrode 108 and its substrate is to ensure the wettability of the electrode 108 in order to have continuous gas generation since the coated electrode can offer better gas solubility comparing to conventional untreated electrode.

To further enhance the electrolysis efficiency, it is effective to change the geometry of electrodes. In some embodiments, inverse-trapezoid electrodes are fabricated via modified standard e-beam lithography or modified photolithography process combined with modified oxygen plasma treatment, modified reactive ion etching (RIE), modified deep reactive ion etching (DRIE), or modified inductive coupled plasma (ICP). Details of fabrication processes are well known in the art and will be omitted herein. On the other hand, the electrolysis efficiency may be enhanced by changing the shape of the electrode. In one embodiment of the invention, the electrode is made in the shape of inverse-trapezoid to generate intense electric field and induce larger amount of gas generation (similar to corona discharge in vacuum).

In one embodiment of the invention, hydrophilic electrodes and substrate can be achieved by hydrophilic treatment such as oxygen plasma treatment, chemical etching, and mechanical rubbing. This hydrophilic treatment can increase pump power efficiency, ensure wettability of the electrode surface, and offer good gas solubility for gas generation. In another embodiment, a superabsorbent material is attached to the surface of the electrode and made of a material selected from PVA poly(vinyl alcohol), PEO poly(ethylene oxide), poly(acrylic acid), PLA (polylactic acid), PGA (polyglycolic acid), PLA/PGA (copolymers) and PCL (polycaprolactone).

Back to the preferred embodiment and referring to FIG. 1 again, the triggering device 125 can be a push button with simple on-off control mechanism for the electronics in the micro delivery device 100. In another embodiment, the triggering device 125 can be a RFID (radio frequency identification), an optical sensor, an acoustic sensor, a magnetic sensor, an on-board timer, a dial, or a wireless timer connection. Any device and method which can trigger the power supply 124 can be used as the triggering device 125 and should not be limited herein. Therefore, with the triggering device 125 described above, the delivering of a therapeutic agent can be controlled on demand.

In still another embodiment, the triggering device 125 can be designed to have pre-programmed therapeutic agent releasing mechanism. By pre-programing a fixed volume of a therapeutic agent for each delivering process, a user (such as a patient or a physician) can access the triggering device 125 multiple times in a day to have fixed volume of a therapeutic agent. This delivering strategy is especially helpful for simple administration scheme subscribed by physician if a fixed bolus volume is enough for the disease treatment. The delivery scheme described herein also makes the micro delivery device 100 costs down.

Figure 8:
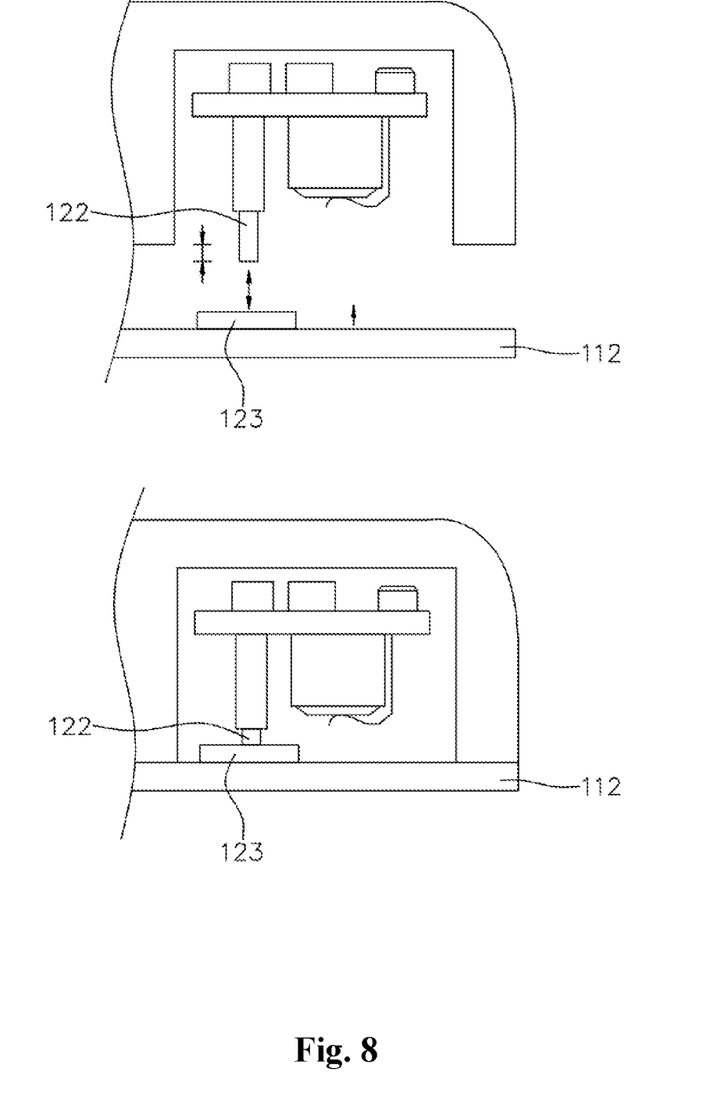
FIG. 8 is a schematic cross-sectional diagram of an electronic device chamber with emphasis on an elastic contactor in one embodiment of the present invention.

Referring to FIG. 8 providing a schematic cross-sectional diagram of an electronic device chamber with emphasis on an elastic contactor in one embodiment of the present invention, the elastic contactor 122 serves as an electrical bridge between the electronics (including the printed circuit board 120, the triggering device 125, and the power supply 124) and the electrode 108. The elastic contactor 122 can be a micro connector such as spring-loaded probe or Pogo Pin (a novel method to achieve the connection in a simple and quick way).

Taking Pogo Pin as an example, this low cost and small component is in a surface-mounted scale and is easy to manipulate even in manual assembly process. FIG. 8 shows that when the substrate 112 is connected to the electronic device chamber 110, the elastic contactor 122 will press on a contact pad 123 and is secured on the substrate 112 to achieve good contact since due to an elastic element (such as a spring) inside the elastic contactor which can give it a push for secure contact. The electric power can pass through the contact pad 123 and go through the substrate 112 to reach the electrode 108 in the lower reservoir 104.

As a result, the elastic contactor 122 in this embodiment not only exhibits simple assembly and easy manufacturing, but also obtains good electrical contact. Moreover, the assembly of elastic contactor 122 in this embodiment can also reduce costs.

Figure 9:
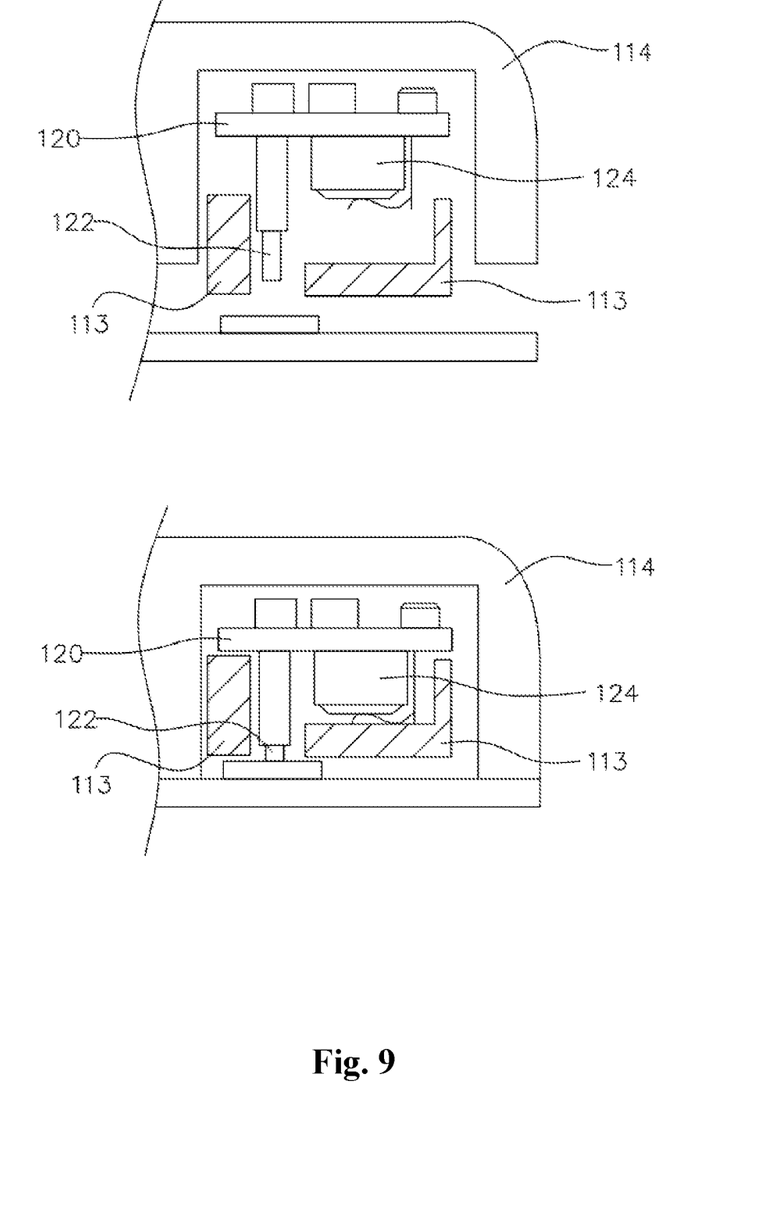
FIG. 9 is a schematic diagram of an electronic device chamber with filler blocks filling in its empty spaces in one embodiment of the present invention.

In another embodiment of the present invention, the electronic device chamber 110 can further includes a filler block 113 filling the empty space in the electronic device chamber 110. Referring to FIG. 9, provided is a schematic diagram of an electronic device chamber with filler blocks filling in its empty spaces in one embodiment of the present invention. In this embodiment, the filler block 113 can be PCB spacers. The filler block 13 can secure electronic components (such as the printed circuit board 120, the power supply 124, and the elastic contactor 122 as shown in the figure). Securing components in this way can replace conventional fixing elements such as screws and clamps, so as to be quick and easy while assembling the whole device.

Some modifications to the preferred embodiment are shown here to give more examples of real applications in order to fit customized demand.

Figure 10:
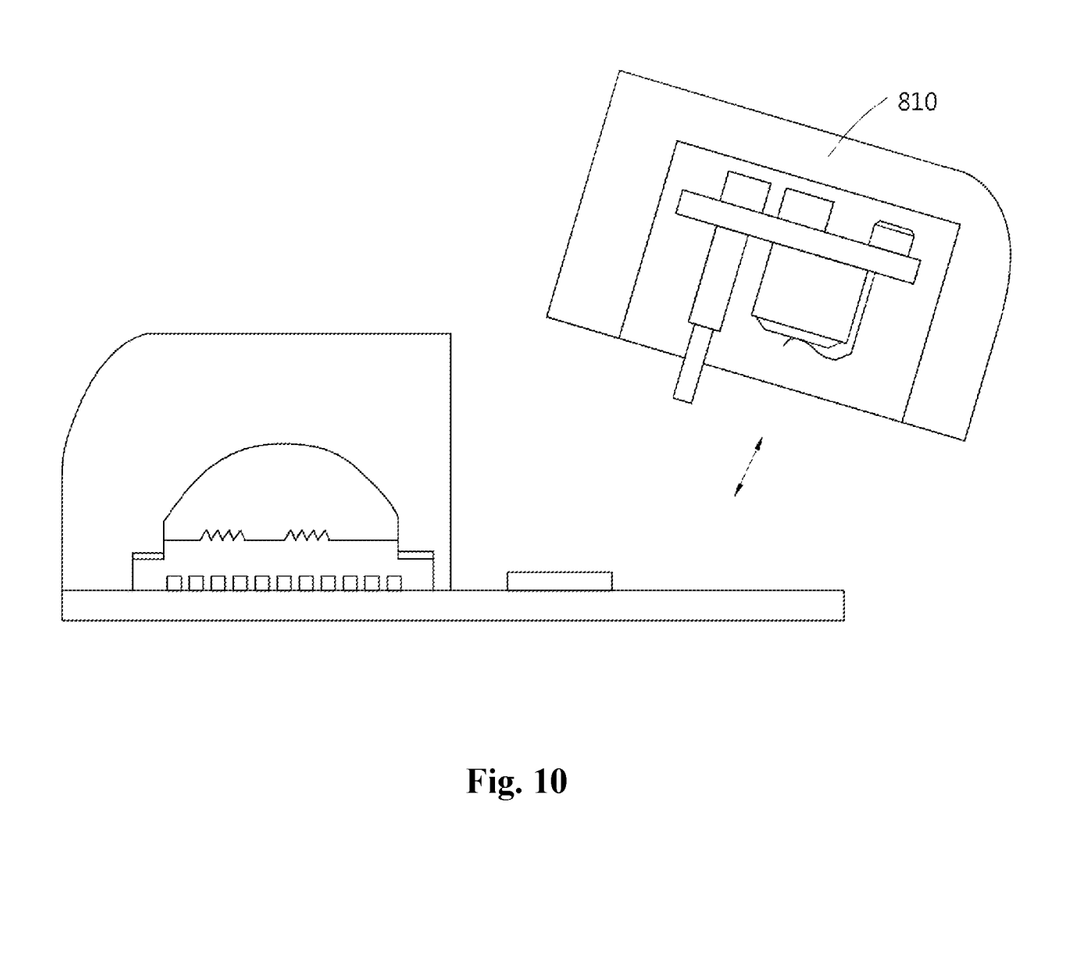
FIG. 10 is a schematic diagram of a modularized micro delivery device in one embodiment of the present invention.

In one modified embodiment, a modularized micro delivery device 800 is demonstrated. FIG. 10 demonstrates a configuration of an assembly of demountable electronic device chamber 810. Referring to FIG. 10 providing a schematic diagram of a modularized micro delivery device in one embodiment of the present invention, only the removable electronic device chamber 810 is swapped whenever the power supply therein is running out of power (or malfunction), which extends the lifetime of the whole device and renders a reusable condition convenient for applications such as chronic disease treatments.

Figure 11:
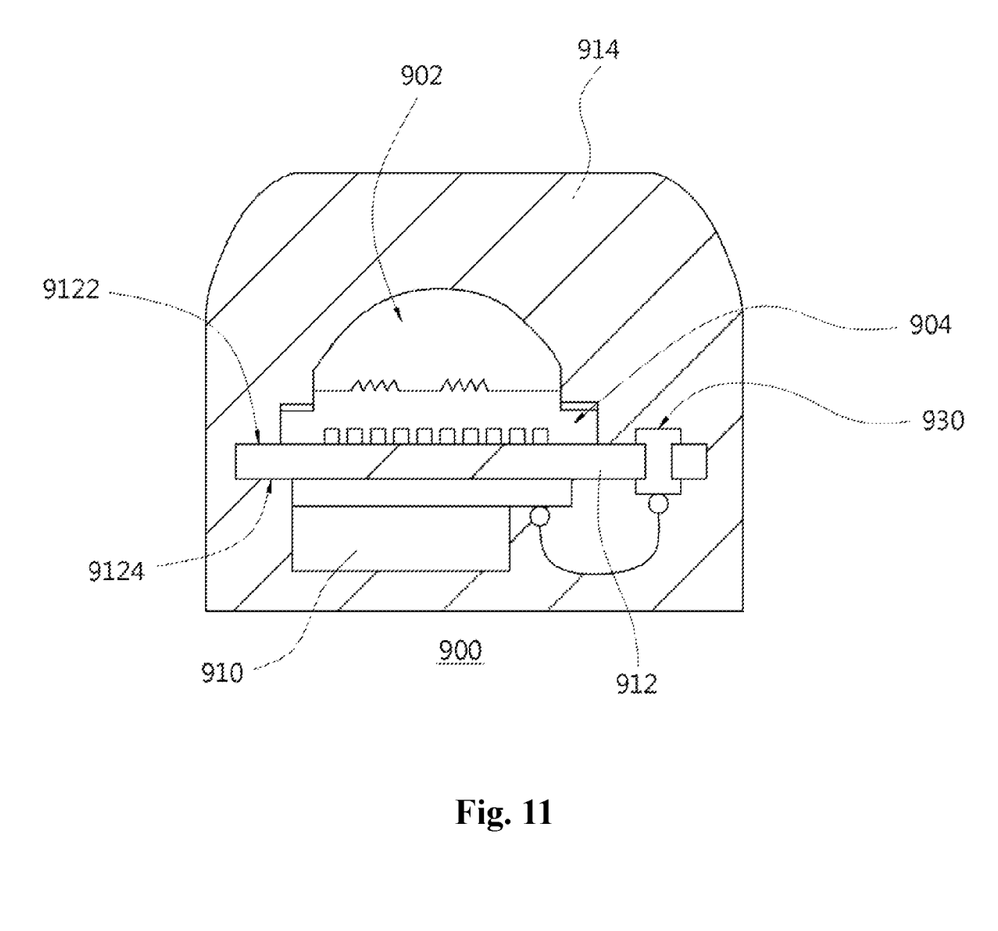
FIG. 11 is a schematic diagram of a micro delivery device in one embodiment of the invention.

In another modified embodiment, the arrangement of chambers can be adjusted such that a substrate serves as a partition plate. Referring to FIG. 11 providing a schematic diagram of a micro delivery device in one embodiment of the invention, a micro delivery device 900 comprises an upper reservoir 902, a lower reservoir 904, an electronic device chamber 910, and a substrate 912. The upper reservoir 902 and the lower reservoir 904 are set on one first side 9122 of the substrate 912, whereas the electronic device chamber 910 is set on the second side 9124 of the substrate 912. The electrical connection between the first side 9122 and the second side 9124 of the substrate 812 can be done by using a feedthrough (via) technique which is widely used in CMOS processes and IC packaging techniques. In this arrangement, the complete separation of "wet" structures from "dry" structures can be done to enhance the liability of the whole device.

It should be mentioned that all of the above-mentioned embodiments can be integrated with standard CMOS processes since MEMS micro electrode micromachining processes used in embodiments of the present invention can be compatible with standard CMOS processes. In conclusion, the advantages of the present invention are described as follows.

First, embodiments of the present invention disclosed herein can greatly improve dosing accuracy and pump structure reliability for the electrolysis-based micropump devices making the overall pump system with longer life cycle, smaller pump footprint, simple in production and low manufacturing cost. Previously, drug delivery pump devices are made in soft reservoir rigid shell materials to make the refilling process easy with one port structure. This rigid shell material design has also applied to the case of the prior micro electrolysis-based pumps. However, the thin soft reservoir rigid shell for these micro pump devices is with rigid shell thickness less than 30 um (0.03 mm) that can be easily over expanded during refilling process if slightly over volume of the therapeutic agent is pushed into the reservoir creating a permanent deformation of the rigid shell. This permanent material deformation raises a serious safety concern for the pharmaceutical industry due to the strict regulatory requirement for dosing control accuracy of the therapeutic agents intended to be used in human. For devices targeting long-term implant applications, a gradual expansion of the materials can sum up to a large dosing inaccuracy, eventually, after years of refilling cycles. In the most deadly case, a fatal error of rupturing the reservoir can occur from either refilling machine system error or human mistakes from an intentional/careless medical operator. Therefore, the rigid shell design in the current invention makes the pump structure much robust and rigid shell is definitely more accurate in verifying the amount of dosage of the therapeutic agent as compared to elastic shells used in conventional ways.

Second, the current invention is the power efficiency for this rigid shell design. For the rigid shell electrolysis pump, during the recombination or slow escaping diffusion of the gases from the pump, in either way, the disappearing of gases creates a vacuum in the pump reservoir. In the successive delivery cycle, the pump has to overcome this previous generated vacuum before the drug can be delivered out of the reservoir. Additional energy supply is required resulting in lower pump energy efficiency and shorter battery lifetime. This lower pump energy efficiency will get worse if the thin rigid shell is with gradual permanent deformation as previously discussed. Therefore, rigid shell design can completely remove this concern and make the pump delivery much accurate with excellent power efficiency rigid shell.

Third, a one-port design for the rigid shell micro pump delivery device with an improved therapeutic agent-refilling method. The rigid shell will lead to an easy determination on the validity of the micro delivery device for withdrawing/refilling a therapeutic agent. However, in prior art, drug delivery pump with rigid shell design are with two refilling ports: one for the evacuation of the remaining/old therapeutic agent and air bubbles in reservoir and the other for refilling the new therapeutic agent. The current invention saves one refilling port compared to other previous rigid pump by using a new therapeutic agent-refilling method including: inserting a syringe connected to an evacuated device into the upper reservoir through the port; turning on the evacuated device to withdraw the therapeutic agent left in the previous dose and air inside the upper reservoir; extracting the syringe from the upper reservoir after the upper reservoir being completely emptied; pre-filling a refilling-syringe with the therapeutic agent and inserting the refilling-syringe into the upper reservoir through the port; and filling a specified dose of the therapeutic agent into the upper reservoir by the refilling-syringe, and extracting the refilling-syringe from the upper reservoir through the port after the filling of the therapeutic agent. By saving one refilling port in the current rigid shell design, it saves the overall device footprint, simplifies the manufacturing steps, and most importantly, and lowers the manufacturing cost.

Fourth, a portless pump can be used for specific implantable pump applications (such as single-used animal pump) where only one initial filling step is required. Without the port, the initial agent filling method includes attaching the needle of a syringe (installed in an evacuated device) to the end of the cannula connecting to the upper reservoir; turning on the evacuated device to withdraw the therapeutic agent left in the previous dose and air inside the upper reservoir; detaching the syringe from the cannula of the upper reservoir after the upper reservoir being completely emptied; pre-filling a refilling-syringe with the therapeutic agent and attaching the needle of a syringe (installed in an evacuated device) to the end of the cannula connecting to the upper reservoir; and filling a specified dose of the therapeutic agent into the upper reservoir by the refilling-syringe, and detaching the refilling-syringe from the cannula of the upper reservoir after the filling of the therapeutic agent. By completely removed the port, the footprint, manufacturing steps, and cost of the pump are minimized.

Fifth, this initial therapeutic agent filling method for the portless pump can be easily operated manually by medical staff with minimal training required.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any appropriate suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A micro delivery device comprising:
   a substrate having a first side and a second side, wherein the second side is opposite to the first side;
   a rigid shell disposed on the first side of the substrate, and a chamber defined by the rigid shell and the substrate;
   a diaphragm configured within the chamber to divide the chamber into an upper reservoir configured to be a storage chamber of a therapeutic agent and a lower reservoir configured to be an electrolysis chamber;
   a cannula penetrating through the rigid shell and in fluid communication with the upper reservoir;
   an electrochemical pump comprising at least one electrode wherein the at least one electrode is disposed on the first side of the substrate; and
   an electronic device chamber electrically connecting to the at least one electrode;

wherein the micro delivery device comprises a single port configured to refill and/or withdraw the therapeutic agent, wherein the upper reservoir consists of part of the rigid shell and part of the diaphragm and the therapeutic agent directly contacts with the rigid shell, and wherein the diaphragm has a helically corrugated structure.

2. The micro delivery device of claim 1, wherein the at least one electrode includes not less than three electrodes, two of the electrodes are applied as positive and negative, one of the electrodes is applied as a reference electrode to prevent IR drop.

3. The micro delivery device of claim 1, wherein the at least one electrode is hydrophilic.

4. The micro delivery device of claim 1, wherein a superabsorbent material is attached to a surface of the at least one electrode.

5. The micro delivery device of claim 4, wherein the superabsorbent material is made of a material selected from PVA poly(vinyl alcohol), PEO poly(ethylene oxide), poly(acrylic acid), PLA (polylactic acid), PGA (polyglycolic acid), PLA/PGA (copolymers) and PCL (polycaprolactone).

6. The micro delivery device of claim 1, wherein the substrate is hydrophilic.

7. The micro delivery device of claim 1, wherein the electronic device chamber is configured on the first side or the second side of the substrate.

8. The micro delivery device of claim 1, wherein the electronic device chamber comprises a printed circuit board, a power supply, a triggering device, and an elastic contactor, the elastic contactor electrically connecting the printed circuit board to the substrate, the power supply being electrically connected to the printed circuit board, and the triggering device being electrically connected to the printed circuit board.

9. The micro delivery device of claim 8, wherein the elastic contactor is a pogo pin.

10. The micro delivery device of claim 1, wherein the electronic device chamber is a demountable electronic device chamber.

11. The micro delivery device of claim 1, wherein the rigid shell is transparent.

12. The micro delivery device of claim 1, wherein the substrate is transparent.

13. The micro delivery device of claim 1, wherein the rigid shell is made of a material selected from PEEK, polycarbonate, parylene, polypropylene, PE, epoxy, PS, PU, ABS, PMMA, PTFE, Teflon, PF, polyimide, PLA, silicone, and glass.

14. The micro delivery device of claim 1, wherein the substrate is made of a material selected from silicon, metals and metal alloys, silicone, parylene, plastics, and glass.

15. The micro delivery device of claim 1, wherein the substrate is flexible.

16. The micro delivery device of claim 1, wherein the substrate is rigid.

17. The micro delivery device of claim 1, wherein the micro delivery device is coated with silicone rubber.

18. The micro delivery device of claim 1, wherein the at east one electrode is made in the shape of an inverse-trapezoid.

19. The micro delivery device of claim 1, wherein the electronic device chamber further comprises a filler block, and the filler block fills an empty space of the electronic device chamber.

20. The micro delivery device of claim 1, wherein a side wall of the cannula has corrugated structures for releasing stress induced from a movement of the micro delivery device.

21. The micro delivery device of claim 1, further comprising a check valve in the cannula or the rigid shell.

22. The micro delivery device of claim 1, wherein the at least one electrode includes more than three electrodes, two of the electrodes are applied as positive and negative, one of the electrodes is applied as a reference electrode to prevent IR drop, and others of the electrodes are used as redundant electrodes to prevent from inconvenience of repairing whenever a sudden malfunction of one of the at least one electrodes occurs.

* * * * *